US012616364B2

(12) United States Patent
Shallik et al.

(10) Patent No.: US 12,616,364 B2
(45) Date of Patent: May 5, 2026

(54) VIDEOLARYNGOSCOPY DEVICE FOR ENDOTRACHEAL INTUBATION

(71) Applicant: Hamad Medical Corporation, Doha (QA)

(72) Inventors: Nabil Shallik, Doha (QA); Yasser Al Hamidi, Doha (QA)

(73) Assignee: HAMAD MEDICAL CORPORATION, Doha (QA)

( * ) Notice: Subject to any disclaimer, the term of this patent is extended or adjusted under 35 U.S.C. 154(b) by 50 days.

(21) Appl. No.: 18/294,462

(22) PCT Filed: Aug. 31, 2022

(86) PCT No.: PCT/QA2022/050016
§ 371 (c)(1),
(2) Date: Feb. 1, 2024

(87) PCT Pub. No.: WO2023/033665
PCT Pub. Date: Mar. 9, 2023

(65) Prior Publication Data
US 2024/0407638 A1      Dec. 12, 2024

Related U.S. Application Data

(60) Provisional application No. 63/239,480, filed on Sep. 1, 2021.

(51) Int. Cl.
A61B 1/267        (2006.01)
A61B 1/00        (2006.01)
(Continued)

(52) U.S. Cl.
CPC .......... A61B 1/267 (2013.01); A61B 1/00052 (2013.01); A61B 1/00055 (2013.01);
(Continued)

(58) Field of Classification Search
CPC ...................................................... A61B 1/267
See application file for complete search history.

(56) References Cited

U.S. PATENT DOCUMENTS 4,295,465 A * 10/1981 Racz ...................... A61B 1/267
                                                                   600/199
4,384,570 A *  5/1983 Roberts .................... A61B 1/07
                                                                   600/187
(Continued)

OTHER PUBLICATIONS

International Search Report for related International Application No. PCT/QA2022/050016; action dated Mar. 9, 2023; (2 pages).
(Continued)

*Primary Examiner* — Tessa M Matthews
(74) *Attorney, Agent, or Firm* — K&L Gates LLP

(57)        ABSTRACT

A medical device for video laryngoscopy is provided. The medical device includes a main body and a pressure sensor module coupled to the main body. The main body includes a base portion having a first inner side facing a first direction and a first outer side opposite the first inner side and facing a second direction. The base portion has a first base end portion and a second base end portion opposite the first base end portion. The medical device further includes a blade portion extending from the second base end portion of the base portion. The medical device also includes a movable tip disposed at the second blade end portion. The movable tip is movable relative to the blade portion between a first position and a second position. The movable tip is configured to bend toward the base portion when transitioned from the first position to the second position.

18 Claims, 9 Drawing Sheets

(51) Int. Cl.
    *A61B 1/012*        (2006.01)
    *A61B 1/04*         (2006.01)

(52) U.S. Cl.
    CPC ...... *A61B 1/00066* (2013.01); *A61B 1/00097*
        (2022.02); *A61B 1/00105* (2013.01); *A61B*
        *1/00114* (2013.01); *A61B 1/012* (2013.01);
                     *A61B 1/04* (2013.01)

(56)             References Cited

U.S. PATENT DOCUMENTS

| | | | |
|---|---|---|---|
| 5,536,245 A | 7/1996 | Dahlbeck | |
| 6,106,458 A | 8/2000 | Ha | |
| 6,174,281 B1 * | 1/2001 | Abramowitz | ........ A61B 1/2673 |
| | | | 600/199 |
| 2005/0187434 A1 | 8/2005 | Dey | |
| 2011/0245609 A1 * | 10/2011 | Laser | ................. A61B 1/00052 |
| | | | 600/109 |
| 2017/0105614 A1 | 4/2017 | Mcwilliam et al. | |
| 2018/0168433 A1 | 6/2018 | Meyer et al. | |

OTHER PUBLICATIONS

Written Opinion for related International Application No. PCT/
QA2022/050016; action dated Mar. 9, 2023; (6 pages).

* cited by examiner

VIDEOLARYNGOSCOPY DEVICE FOR ENDOTRACHEAL INTUBATION

PRIORITY CLAIM

The present application is a National Stage filing under 35 U.S.C. 371 of International Application No. PCT/QA2022/050016, filed Aug. 31, 2022, which claims priority to and the benefit of U.S. Provisional Patent Application No. 63/239,480, filed on Sep. 1, 2021, the entirety of which is incorporated herein by reference.

BACKGROUND

Videolaryngoscopy is a form of indirect laryngoscopy in which the clinician does not directly view the larynx. The images from videolaryngoscopy can be displayed, magnified, and recorded on a monitor.

SUMMARY

The present disclosure generally relates to a videolaryngoscopy device or system for endotracheal intubation.

In light of the present disclosure, and without limiting the scope of the disclosure in any way, in an aspect of the present disclosure, which may be combined with any other aspect listed herein unless specified otherwise, a medical device for videolaryngoscopy is provided. The medical device includes a main body and a pressure sensor module coupled to the main body. The main body includes a base portion having a first inner side facing a first direction and a first outer side opposite the first inner side and facing a second direction. The base portion has a first base end portion and a second base end portion opposite the first base end portion. The medical device further includes a blade portion extending from the second base end portion of the base portion. The blade portion includes a first blade end portion adjacent the second base end portion and a second blade end portion opposite the first blade end portion. The blade portion is bent from the base portion toward the first direction. The medical device also includes a movable tip disposed at the second blade end portion. The movable tip has a first tip end portion adjacent the second blade end portion and a second tip end portion opposite the first tip end portion. The movable tip is movable relative to the blade portion between a first position and a second position. The movable tip is configured to bend toward the base portion when transitioned from the first position to the second position. The pressure sensor module includes a pressure sensor and is configured to detect a pressure applied to the pressure sensor.

In an aspect of the present disclosure, which may be combined with any other aspect listed herein unless specified otherwise, the first outer side of the base portion comprises a first recess configured to receive the pressure sensor module.

In an aspect of the present disclosure, which may be combined with any other aspect listed herein unless specified otherwise, the pressure sensor module is removably coupled to the main body.

In an aspect of the present disclosure, which may be combined with any other aspect listed herein unless specified otherwise, the blade portion has a second inner side and a second outer side opposite the second inner side, wherein the second outer side of the blade portion comprises a second recess configured to receive the pressure sensor.

In an aspect of the present disclosure, which may be combined with any other aspect listed herein unless specified otherwise, the second recess is disposed adjacent the first blade end portion.

In an aspect of the present disclosure, which may be combined with any other aspect listed herein unless specified otherwise, the main body further comprises an oxygen passage formed internally, wherein the oxygen passage is configured to transmit oxygen to a patient during a medical procedure.

In an aspect of the present disclosure, which may be combined with any other aspect listed herein unless specified otherwise, the oxygen passage extends from the first base end portion to the second blade end portion.

In an aspect of the present disclosure, which may be combined with any other aspect listed herein unless specified otherwise, the oxygen passage extends from the first base end portion to the second tip end portion.

In an aspect of the present disclosure, which may be combined with any other aspect listed herein unless specified otherwise, the oxygen passage is configured to be coupled to an oxygen source from which the oxygen is supplied to the patient through the oxygen passage.

In an aspect of the present disclosure, which may be combined with any other aspect listed herein unless specified otherwise, the oxygen passage is configured to receive a camera cable.

In an aspect of the present disclosure, which may be combined with any other aspect listed herein unless specified otherwise, the pressure sensor module is configured to generate a notification signal when a pressure greater than a predetermined amount is detected.

In an aspect of the present disclosure, which may be combined with any other aspect listed herein unless specified otherwise, the notification signal comprises a light signal.

In an aspect of the present disclosure, which may be combined with any other aspect listed herein unless specified otherwise, the medical device further comprises a trigger configured to move the movable tip between the first position and the second position.

In an aspect of the present disclosure, which may be combined with any other aspect listed herein unless specified otherwise, the trigger is disposed in the base portion of the main body.

In an aspect of the present disclosure, which may be combined with any other aspect listed herein unless specified otherwise, the medical device further comprises a link connecting the trigger to the movable tip.

In an aspect of the present disclosure, which may be combined with any other aspect listed herein unless specified otherwise, the medical device further comprises a retractable biasing device coupled to the trigger, wherein the trigger is configured to move between a default position and an actuated position, wherein the retractable biasing device is configured to move the trigger from the actuated position to the default position.

In an aspect of the present disclosure, which may be combined with any other aspect listed herein unless specified otherwise, the medical device further comprises a display device disposed on the base portion.

In an aspect of the present disclosure, which may be combined with any other aspect listed herein unless specified otherwise, the display device comprises a mobile device.

In an aspect of the present disclosure, which may be combined with any other aspect listed herein unless specified otherwise, the display device is disposed adjacent the first base end portion.

In light of the present disclosure, and without limiting the scope of the disclosure in any way, in an aspect of the present disclosure, which may be combined with any other aspect listed herein unless specified otherwise, a medical device system is provided. The medical device includes a main body and a pressure sensor module coupled to the main body. The main body includes a base portion having a first inner side facing a first direction and a first outer side opposite the first inner side and facing a second direction. The base portion has a first base end portion and a second base end portion opposite the first base end portion. The medical device further includes a blade portion extending from the second base end portion of the base portion. The blade portion includes a first blade end portion adjacent the second base end portion and a second blade end portion opposite the first blade end portion. The blade portion is bent from the base portion toward the first direction. The medical device also includes a movable tip disposed at the second blade end portion. The movable tip has a first tip end portion adjacent the second blade end portion and a second tip end portion opposite the first tip end portion. The movable tip is movable relative to the blade portion between a first position and a second position. The movable tip is configured to bend toward the base portion when transitioned from the first position to the second position. The pressure sensor module includes a pressure sensor and is configured to detect a pressure applied to the pressure sensor. The medical device further includes a display device holder disposed on the base portion and configured to hold a display device.

The reader will appreciate the foregoing details, as well as others, upon considering the following detailed description of certain non-limiting embodiments including a medical device for videolaryngoscopy according to the present disclosure.

4

Figure 8:
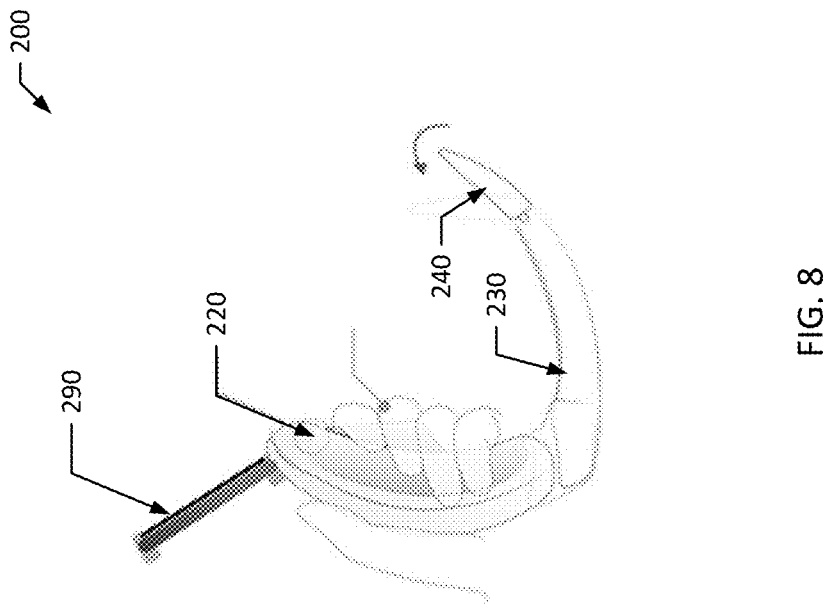

FIG. 8 is a diagram of a medical device for videolaryngoscopy according to another example embodiment of the present disclosure.

Figure 9:
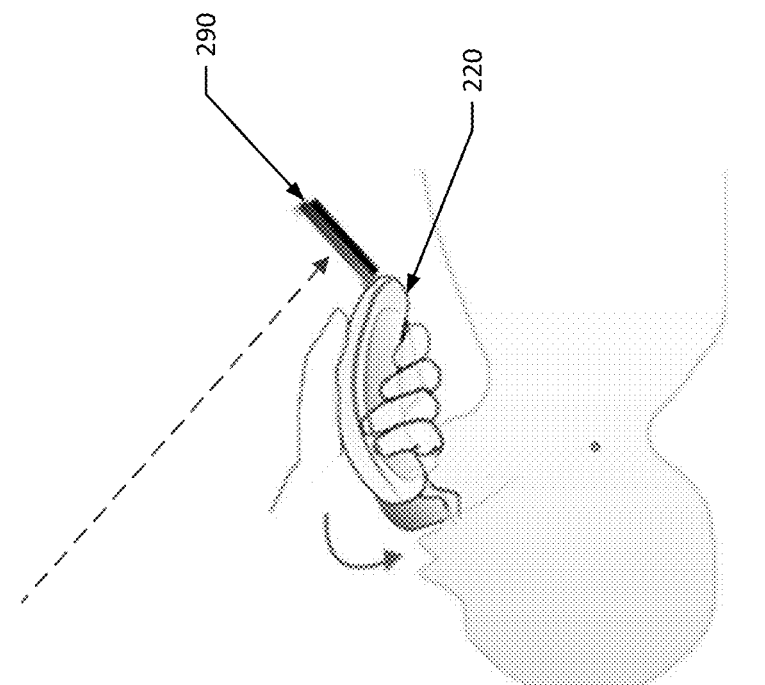

FIG. 9 is a diagram of a medical device for videolaryngoscopy used for treating a patient according to another example embodiment of the present disclosure.

DETAILED DESCRIPTION

The present disclosure generally relates to a medical device and system for videolaryngoscopy.

The conventional videolaryngoscopy devices have various disadvantages. For example, oxygenation may be disturbed during intubation. Iatrogenic injury can also occur while intubating patients during procedures requiring general anesthesia. For example, emergent and difficult tracheal intubations may be hazardous undertakings where successive laryngoscopy-hypoxaemia-reoxygenation cycles can escalate to airway loss and the "can't intubate, can't ventilate" scenario. As the patient transitions from wakefulness to anesthesia, and receives neuromuscular blockade, the anesthetist may be given a finite time ('apneic window') during which to secure a definitive airway. Failure to do so may result in recommencement of facemask ventilation, reoxygenation and a further attempt at securing a definitive airway. In some patients, the combination of unfavorable pharyngo-laryngeal anatomy and reduced apnea time due to cardiorespiratory decompensation may make this stop-start approach hazardous. Multiple attempts at difficult laryngoscopy may increase the risk of airway trauma, which in turn makes subsequent attempts at laryngoscopy and facemask ventilation more difficult. This can deleteriously impact on human factors that are intrinsic to a highly pressured clinical scenario, and can readily cascade into a "cannot intubate, cannot ventilate" scenario with significant attending morbidity and mortality.

Iatrogenic injury can also occur while intubating patients during procedures requiring general anesthesia. General anesthesia involves instrumentation that can injure soft tissues and dental tissues by pressure during intubation. For example, upper incisors can be damaged if not used properly.

Fixed tip laryngoscopy may also create issues during intubation of the trachea, for example, in a patient with a potential cervical spine injury. Immobilization of the neck in a neutral position may make the view at laryngoscopy more difficult.

Aspects of the present disclosure may address the above-discussed issues in the conventional videolaryngoscopy devices. For example, according to an embodiment of the present disclosure, a medical device for videolaryngoscopy may include a movable tip. The movable tip may be connected through a strong metal link to a trigger button. The trigger button may be placed at an appropriate and convenient height to be spaced apart from the patient's mouth during a medical procedure. The position and the length of the trigger may be carefully selected to have the trigger extended across the entire breadth of the palm to avoid causing any unnecessary compression in the middle portion of the operator's palm.

The movable tip at an end of the blade of the medical device may decrease pressure on the teeth as fulcrum during exploration of the epiglottis. The movable tip at the end of blade may also decrease extension of the neck during exploration of the epiglottis and decrease the hyperextension of the cervical spine. In this case, the epiglottis can be easily elevated without stressful force to the upper incisors or stressful neck extension, and this may help a lot for laryngeal visualization in patients with limited neck extension and difficult intubation.

The medical device may also include a main body serving as a path for the oxygen passage, a camera, and an intubation guide. The oxygen passage/channel may be used for continuous $O_2$ supply to keep the patient always oxygenated during all procedures. In some examples, the oxygen passage/channel may direct the oxygen jet flow through a suction port around the lens, which may remove camera fogging issues.

The medical device may also include a pressure sensor module. The pressure sensor module may be slidably inserted into the main blade body and generate an alarm upon excessive force. The pressure sensor in the blade may generate an alarm when excessive pressure is used during intubation. The pressure sensor may detect different levels of contact forces that can be shown to the operator, for example, via a change in LED indicator color depending on the force. In some examples, the pressure sensor and its associated electronics board may be designed as a separate module that can be slid into the main blade body for easy repair and replacement.

In some examples, a mobile phone and/or a mobile application may be used to view and record the video of endotracheal intubation and/or share the video with other devices via Bluetooth or Wi-Fi connections. In other examples, the medical device may include a separate display device configured to display the video of endotracheal intubation and a processing unit (e.g., a processor and a memory) configured to record the video of endotracheal intubation and/or share the video with other devices, for example, via Bluetooth or Wi-Fi connections.

Figure 1:
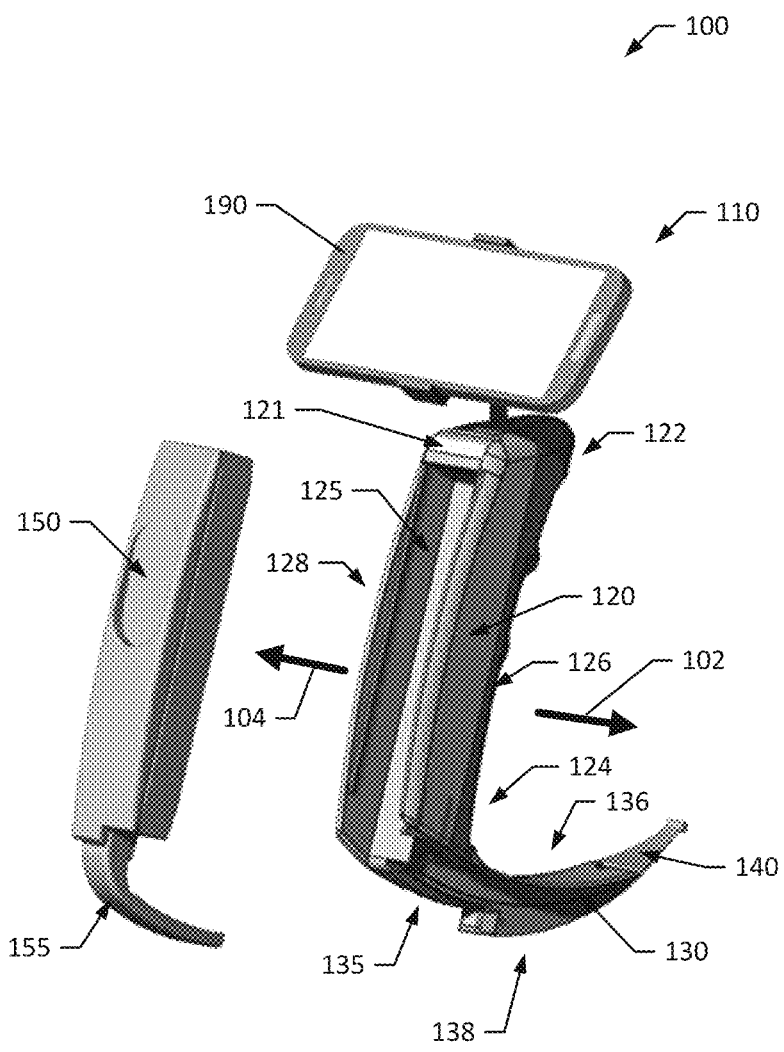
FIG. 1 is a diagram of a front-right perspective view of a medical device for videolaryngoscopy when a pressure sensor module is detached from a main body according to an example embodiment of the present disclosure.
Figure 2:
FIG. 2 is a diagram of a front-right perspective view of the medical device of FIG. 1 when the pressure sensor module is coupled with the main body.
Figure 2:
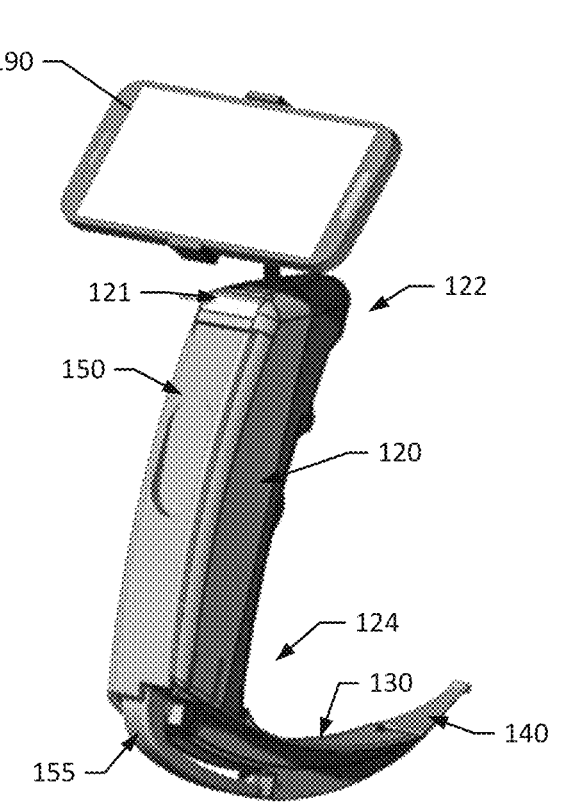
Figure 3:
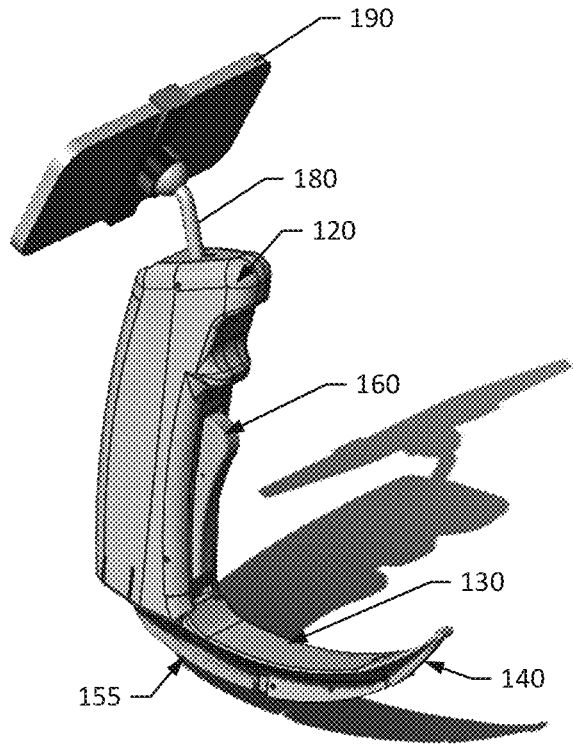
FIG. 3 is a diagram of a rear-left perspective view of the medical device of FIG. 1 when the pressure sensor module is coupled with the main body.
Figure 4:
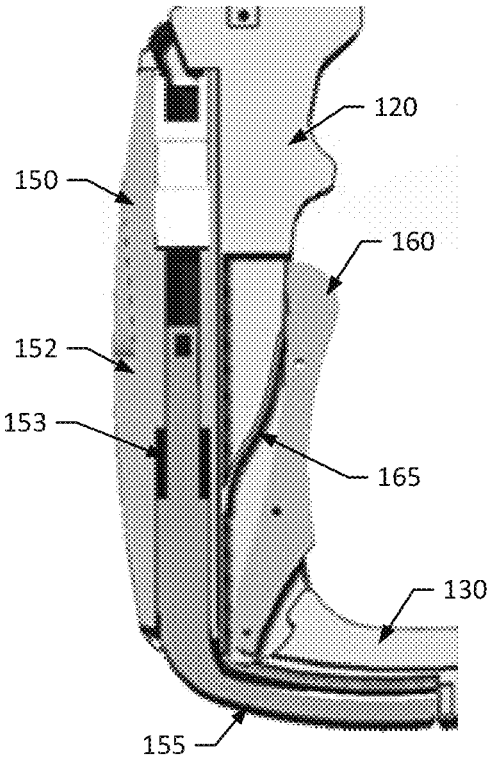
FIG. 4 is a diagram of a partial sectional view of the pressure sensor module and the area surrounding the pressure sensor module of the medical device of FIG. 1 when the pressure sensor module is coupled with the main body.
Figure 5:
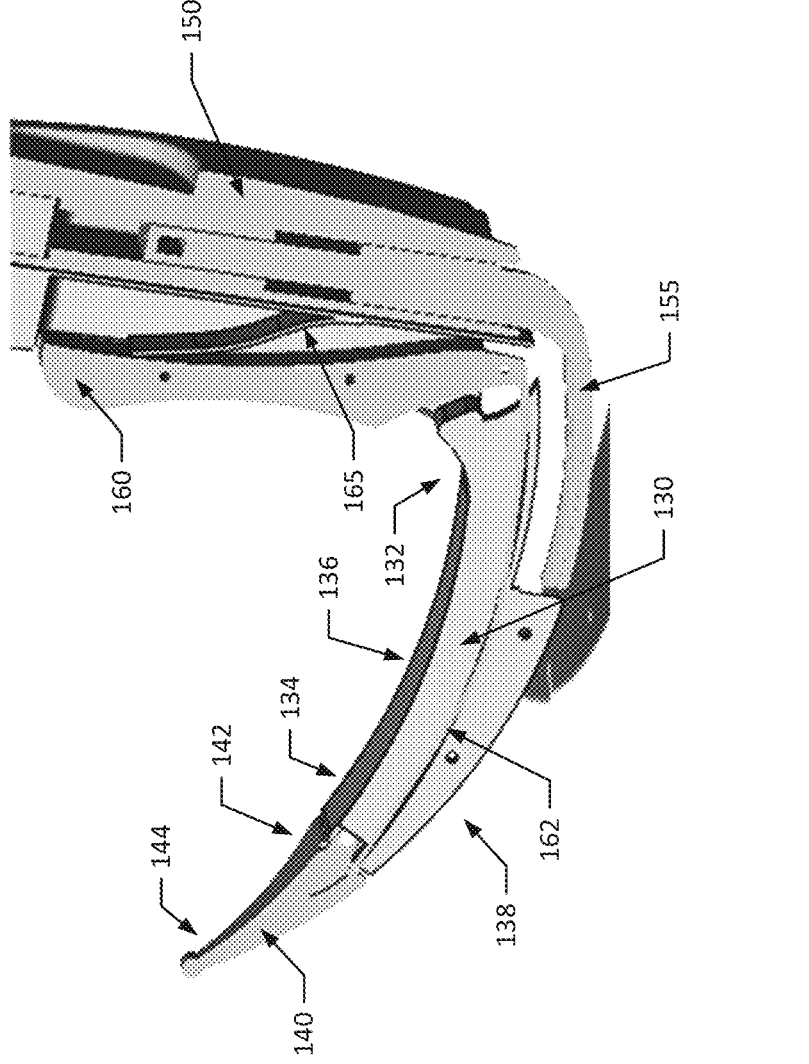
FIG. 5 is a diagram of a partial sectional view of the medical device of FIG. 1 when the pressure sensor module is coupled with the main body.

FIG. 1 is a diagram of a front-right perspective view of a medical device 100 for videolaryngoscopy when a pressure sensor module is detached from a main body according to an example embodiment of the present disclosure. FIG. 2 is a diagram of a front-right perspective view of the medical device 100 of FIG. 1 when the pressure sensor module is coupled with the main body. FIG. 3 is a diagram of a rear-left perspective view of the medical device of FIG. 1 when the pressure sensor module is coupled with the main body. FIG. 4 is a diagram of a partial sectional view of the pressure sensor module and the area surrounding the pressure sensor module of the medical device 100 of FIG. 1 when the pressure sensor module is coupled with the main body. FIG. 5 is a diagram of a partial sectional view of the medical device 100 of FIG. 1 when the pressure sensor module is coupled with the main body.

Referring to FIGS. 1 to 5, a medical device 100 according to the present disclosure may include a main body 110. The main body 110 may include a base portion 120. The base portion 120 may have a first inner side 126 facing a first direction 102 and a first outer side 128 opposite the first inner side 126 and facing a second direction 104. The base portion 120 may have a first base end portion 122 and a second base end portion 124 opposite the first base end portion 122. The base portion 120 may serve as a handle to be held by a hand of the user during a medical procedure.

In some examples, the medical device 100 may also include a blade portion 130. The blade portion 130 may extend from the second base end portion 124 of the base portion 120. The blade portion 130 may include a first blade end portion 132 adjacent the second base end portion 124 and a second blade end portion 134 opposite the first blade end portion 132. The blade portion 130 may be bent from the base portion 120 toward the first direction 102. In some examples, the angle formed between the base portion 120 and the blade portion 130 may be in a range of about 75° to about 105°, for example, about 80° to about 100°, about 85° to about 95°, or about 88° to about 92°. In other examples, the base portion 120 and the blade portion 130 may form any other suitable angle.

In some examples, the medical device 100 may also include a movable tip 140. The movable tip 140 may be disposed at the second blade end portion 134. The movable tip 140 may have a first tip end portion 142 adjacent the second blade end portion 134 and a second tip end portion 144 opposite the first tip end portion 142.

Figure 6B:
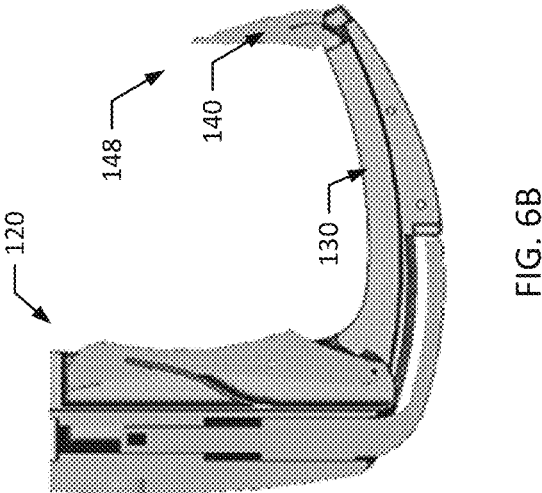
FIG. 6B is a diagram of a partial sectional view of the medical device of FIG. 1 when the movable tip is in a tilted position.
Figure 6A:
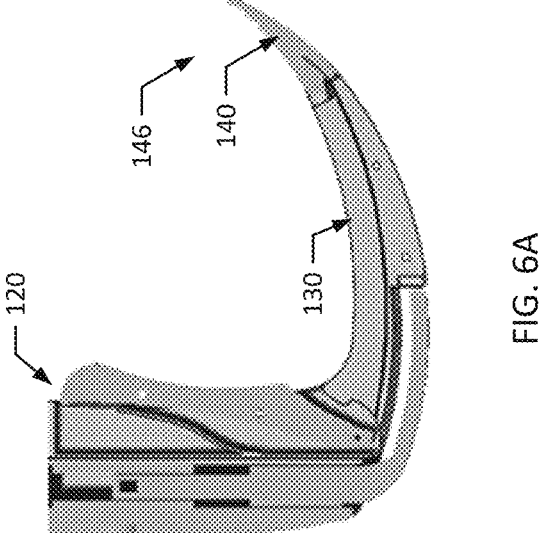
FIG. 6A is a diagram of a partial sectional view of the medical device of FIG. 1 when the movable tip is in a rest position.

The movable tip 140 may be movable relative to the blade portion 130 between a first position and a second position. For example, as illustrated in FIGS. 6A and 6B, the movable tip 140 may be movable between a first position 146 and a second position 147. The first position 146 may be a rest/default position, and the second position 148 may be a tilted/actuated position. As shown in FIGS. 6A and 6B, the movable tip 140 may bend, for example, toward the base portion 120 when the movable tip 140 is transitioned from the first position 146 to the second position 148. In some examples, the bending angle of the movable tip 140 may be in a range of about 60° to about 110°, for example, about 70° to about 100°, about 75° to about 95°, or about 80° to about 90°. In other examples, the movable tip 140 may have any other suitable bending angle.

This configuration of the movable tip 140 at the second blade end portion 134 may decrease pressure on the teeth (e.g., upper incisors) during exploration of the epiglottis. This may also decrease extension of the neck during exploration of the epiglottis and the hyperextension of the cervical spine. By moving the movable tip 140 between the first position 146 and the second position 147, the epiglottis can be easily elevated without stressful force to the upper incisors or stressful neck extension, which may improve the laryngeal visualization in patients with limited neck extension and difficult intubation.

In some examples, the medical device 100 may further include a pressure sensor module 150. In some examples, the pressure sensor module 150 may be removably coupled to the main body 110. The pressure sensor module 150 may include a pressure sensor 155. The pressure sensor module 150 may detect a pressure applied to the pressure sensor 150. In some examples, the first outer side 128 of the base portion 120 may include a first recess 125. The first recess 125 may be configured to receive the pressure sensor module 150.

In some examples, the pressure sensor module 150 may generate a notification signal when a pressure greater than a predetermined amount is detected. In some examples, the notification signal may be in the form of a light signal. In other examples, the notification signal may be in any other suitable form. In some examples, the medical device 100 may include an indicator 121. In some examples, the indicator 121 may be an LED lamp. The pressure sensor 155/pressure sensor module 150 may detect different levels of contact forces that can be shown to the operator via a change in the color of the indicator 121 depending on the force. In other examples, the indicator 121 may be any other suitable device that can give a notification to the user (e.g., any suitable lighting/alarm/audio device). In some examples, the processor sensor 155 may be pressed by the teeth (e.g., upper incisors) of a patient during a medical procedure, and the pressure may be applied by the contact with the teeth. The detection of the pressure applied to the pressure sensor 155 disposed in the first blade end portion 132 may help the user/surgeon avoid damages to the teeth of the patient.

The blade portion 130 may have a second inner side 136 and a second outer side 138 opposite the second inner side 136. In some examples, the second outer side 138 of the blade portion 130 may include a second recess 135. The second recess 135 of the blade portion 130 may be configured to receive the pressure sensor 155. In some examples, the second recess 135 may be disposed adjacent the first blade end portion 132. In other examples, the second recess 135 may be disposed at any other suitable portion of the blade portion 130.

As illustrated in FIG. 4, in some examples, the pressure sensor module 150 may have a sensor base body 152. The sensor base body 152 may be removably inserted into the first recess 125. The sensor base body 152 may serve as a body holding an electronics board (e.g., PCB board) that may receive and process the signals detected and transmitted from the pressure sensor 155. The pressure sensor module 150 (e.g., electronics board) may be in communication with the indicator 121.

The sensor base body 152 may have an internal space 153 for receiving the pressure sensor 155. The pressure sensor 155 may extend from the sensor base body 152 and removably inserted into the second recess 135. As shown in FIG. 4, the pressure sensor 155 may be bent from the sensor base body 152, for example, toward the first direction 102. The bending angle of the pressure sensor 155 may be similar to or same as the angle between the body portion 120 and the blade portion 130. In some examples, the first recess 125 and the second recess 135 may be connected to each other, for example, so that the first and second recesses can receive the sensor base body 152 and the pressure sensor 155 at the same time.

In some examples, the medical device 100 may include a trigger 160. The trigger 160 may move the movable tip 140 between the first position 146 and the second position 148. For example, initially, the trigger 160 may be in a default position, but when the trigger 160 is pressed by a user, it may move from the default position to an actuated position. In some examples, the trigger 160 may be disposed in/on the base portion 120 (e.g., first inner side 126) of the main body 110. In other examples, the trigger 160 may be disposed in any other suitable portion of the medical device 100.

As illustrated in FIG. 5, in some examples, the medical device 100 may also include a link 162. The link 162 may connect the trigger 160 to the movable tip 140. The movement of the trigger 160 (e.g., between the default position and the actuated position) may be transmitted/delivered to the movable tip 140, thereby transitioning the movable tip 140 between the first position 146 and the second position 148. In some examples, the link 162 may be made with a metal material. In other examples, the link 162 may be made with any other suitable material.

In some examples, the medical device 100 may further include a retractable biasing device 165. The retractable biasing device 165 may be coupled to the trigger 160. The retractable biasing device 165 may be configured to move the trigger from the actuated position to the default position. For example, when the pressure applied to the trigger 160, which is in the actuated position due to the pressure, is removed, the retractable biasing device 165 may move the trigger from the actuated position to the default position. An example of the retractable biasing device 165 may include a spring. In other examples, the retractable biasing device 165 may be any other suitable retractable device that can cause the trigger 160 to return to its original/default position when the pressure applied thereto is removed.

Figure 7:
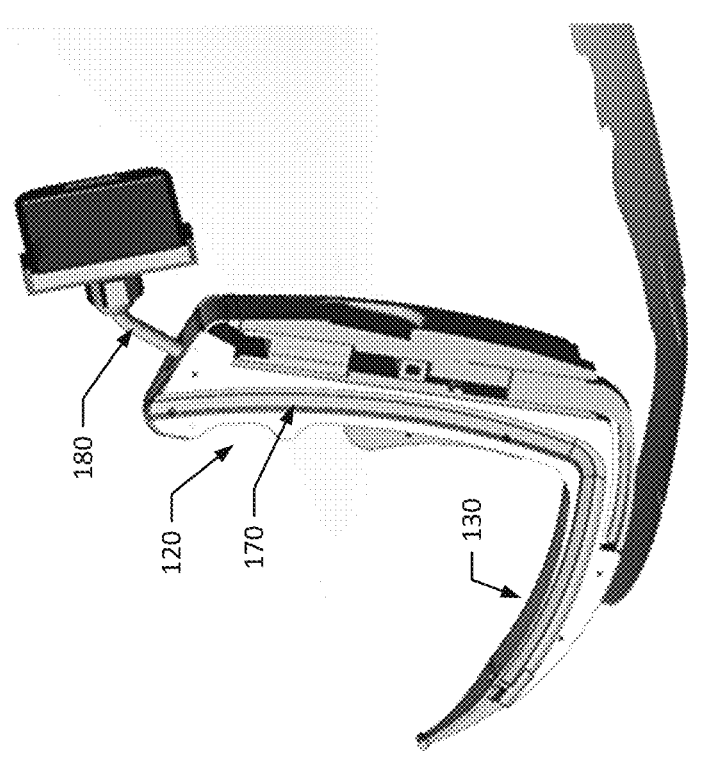
FIG. 7 is a diagram of another partial sectional view of the medical device of FIG. 1, showing an oxygen passage.

As illustrated in FIG. 7, in some examples, the main body 110 may further include an oxygen passage 170 formed internally inside the main body 110. The oxygen passage may be configured to transmit oxygen to a patient, for example, during a medical procedure. In some examples, the oxygen passage 170 may extend from the first base end portion 122 to the second blade end portion 134. In some examples, the oxygen passage 170 may extend from the first base end portion 122 to the second tip end portion 144. The oxygen passage 170 may have an input port near the first base end portion 122. The oxygen passage 170 may have an output port near the second blade end portion 134 or the second tip end portion 144.

In some examples, the oxygen passage 170 may be configured to be coupled to an oxygen source from which the oxygen is supplied to the patient through the oxygen passage 170. For example, the oxygen source may be coupled to the input port of the oxygen passage 170 near the first base end portion 122.

In some examples, in addition to transmitting/delivering the oxygen, the oxygen passage 170 may be also configured to receive a camera cable. That is, the oxygen passage 170 may be shared for the oxygen delivery and a path for the camera cable. The camera cable may include a camera at a distal end of the camera cable. In some examples, the camera may be disposed near the second tip end portion 144. In some examples, this configuration may be used to address the camera fogging issue. For example, the oxygen passage 170 may direct the oxygen jet flow through a suction port around the camera lens, which may remove the camera fog caused by the patient's respiration/secretion/blood.

In some examples, the medical device 100 may further include a display device 190. The display device may be configured to display the video of endotracheal intubation, for example, transmitted from the camera and camera cable. The display device 190 may be disposed on the base portion 120. For example, the display device 190 may be disposed adjacent the first base end portion 122. In some examples, the display device 190 may be a mobile device (e.g., smart phone). In other examples, the display device 190 may be any other suitable device with a display.

In some examples, the display device 190 may further include an application. The display device 190 may be used to view and record, for example, through the application, the video of endotracheal intubation (e.g., transmitted from the camera) and/or share the video with other devices via wired or wireless (e.g., Bluetooth or Wi-Fi) connections. In some examples, the medical device 100 may also include a processing unit (e.g., a processor and a memory) configured to record the video of endotracheal intubation and/or share the video with other devices via wired or wireless connections.

In some examples, the medical device 100 may include a display device holder 180. The display device holder 180 may be disposed on the base portion and configured to hold the display device 190. In some examples, the display device holder 180 can be tilted or rotated so that the user can see the screen of the display device 190 during a medical procedure.

FIG. 8 is a diagram of a medical device 200 for video-laryngoscopy according to another example embodiment of the present disclosure. The medical device 200 may include a main body having a base portion 220, a blade portion 230, and a movable tip 240. The medical device 200 may further include a display device 290. As shown in FIG. 8, in some examples, the medical device 200 and the components thereof (e.g., base portion 220, a trigger) may have an ergonomic design. Other configurations/features/characteristics of the medical device 200 of FIG. 8 (e.g., pressure sensor module, trigger, link, oxygen passage, movable tip movement, etc.) may be similar to and/or same as the ones described above with respect to the medical device 100 of FIGS. 1-7, and, thus, duplicate description may be omitted.

FIG. 9 is a diagram of the medical device 200 for videolaryngoscopy used for treating a patient according to another example embodiment of the present disclosure. As illustrated in FIG. 9, the display device 290 of the medical device 200 may have an angle relative to the base portion 220 so that the user can see the screen of the display device 290 during the medical procedure. In some examples, the angle between the display device 290 and the base portion 220 may be in a range of about 75° to about 150°. In other examples, the base portion 120 and the blade portion 130 may form any other suitable angle. The angle between the display device 290 and the base portion 220 can be adjusted using the display device holder (e.g., tilting the display device holder) on which the display device is placed.

As used herein, "about," "approximately" and "substantially" are understood to refer to numbers in a range of numerals, for example the range of –10% to +10% of the referenced number, preferably –5% to +5% of the referenced number, more preferably –1% to +1% of the referenced number, most preferably –0.1% to +0.1% of the referenced number. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

Reference throughout the specification to "various aspects," "some aspects," "some examples," "other examples," "some cases," or "one aspect" means that a particular feature, structure, or characteristic described in connection with the aspect is included in at least one example. Thus, appearances of the phrases "in various aspects," "in some aspects," "certain embodiments," "some examples," "other examples," "certain other embodiments," "some cases," or "in one aspect" in places throughout the specification are not necessarily all referring to the same aspect. Furthermore, the particular features, structures, or characteristics illustrated or described in connection with one example may be combined, in whole or in part, with features, structures, or characteristics of one or more other aspects without limitation.

When the position relation between two parts is described using the terms such as "on," "above," "below," "under," and "next," one or more parts may be positioned between the two parts unless the terms are used with the term "immediately" or "directly." Similarly, as used herein, the terms "attachable," "attached," "connectable," "connected," or any similar terms may include directly or indirectly attachable, directly or indirectly attached, directly or indirectly connectable, and directly or indirectly connected.

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

The terminology used herein is intended to describe particular embodiments only and is not intended to be limiting of the present disclosure. As used herein, the singular forms "a," "an," and "the" are intended to include the plural forms as well, unless otherwise indicated. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "at least one of X or Y" or "at least one of X and Y" should be interpreted as X, or Y, or X and Y.

It should be understood that various changes and modifications to the examples described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical device for video laryngoscopy, the medical device comprising:

a main body comprising:

a base portion having a first inner side facing a first direction and a first outer side opposite the first inner side and facing a second direction, wherein the base portion has a first base end portion and a second base end portion opposite the first base end portion;

a blade portion extending from the second base end portion of the base portion, wherein the blade portion includes a first blade end portion adjacent the second base end portion and a second blade end portion opposite the first blade end portion, wherein the blade portion is bent from the base portion toward the first direction; and a movable tip disposed at the second blade end portion, wherein the movable tip has a first tip end portion adjacent the second blade end portion and a second tip end portion opposite the first tip end portion, wherein the movable tip is movable relative to the blade portion between a first position and a second position, wherein the movable tip is configured to bend toward the base portion when transitioned from the first position to the second position;

a pressure sensor module coupled to the main body and comprising a pressure sensor, wherein the pressure sensor module is configured to detect a pressure applied to the pressure sensor;

a trigger configured to move the movable tip between the first position and the second position; and a retractable biasing device coupled to the trigger, wherein the trigger is configured to move between a default position and an actuated position, wherein the retractable biasing device is configured to move the trigger from the actuated position to the default position.

2. The medical device according to claim 1, wherein the first outer side of the base portion comprises a first recess configured to receive the pressure sensor module.

3. The medical device according to claim 1, wherein the pressure sensor module is removably coupled to the main body.

4. The medical device according to claim 1, wherein the blade portion has a second inner side and a second outer side opposite the second inner side, wherein the second outer side of the blade portion comprises a second recess configured to receive the pressure sensor.

5. The medical device according to claim 4, wherein the second recess is disposed adjacent the first blade end portion.

6. The medical device according to claim 1, wherein the main body further comprises an oxygen passage formed internally, wherein the oxygen passage is configured to transmit oxygen to a patient during a medical procedure.

7. The medical device according to claim 6, wherein the oxygen passage extends from the first base end portion to the second blade end portion.

8. The medical device according to claim 6, wherein the oxygen passage extends from the first base end portion to the second tip end portion.

9. The medical device according to claim 6, wherein the oxygen passage is configured to be coupled to an oxygen source from which the oxygen is supplied to the patient through the oxygen passage.

10. The medical device according to claim 6, wherein the oxygen passage is configured to receive a camera cable.

11. The medical device according to claim 1, wherein the pressure sensor module is configured to generate a notification signal when a pressure greater than a predetermined amount is detected.

12. The medical device according to claim 11, wherein the notification signal comprises a light signal.

13. The medical device according to claim 1, wherein the trigger is disposed in or on the base portion of the main body.

14. The medical device according to claim 1, further comprising a link connecting the trigger to the movable tip.

15. The medical device according to claim 1, further comprising a display device disposed on the base portion.

16. The medical device according to claim 15, wherein the display device comprises a mobile device.

17. The medical device according to claim 15, wherein the display device is disposed adjacent the first base end portion.

18. A medical device system for video laryngoscopy, the medical device system comprising:

a main body comprising:

a base portion having a first inner side facing a first direction and a first outer side opposite the first inner side and facing a second direction, wherein the base portion has a first base end portion and a second base end portion opposite the first base end portion;

a blade portion extending from the second base end portion of the base portion, wherein the blade portion includes a first blade end portion adjacent the second base end portion and a second blade end portion opposite the first blade end portion, wherein the blade portion is bent from the base portion toward the first direction; and a movable tip disposed at the second blade end portion, wherein the movable tip has a first tip end portion adjacent the second blade end portion and a second tip end portion opposite the first tip end portion, wherein the movable tip is movable relative to the blade portion between a first position and a second position, wherein the movable tip is configured to bend toward the base portion when transitioned from the first position to the second position;

a pressure sensor module coupled to the main body and comprising a pressure sensor, wherein the pressure sensor module is configured to detect a pressure applied to the pressure sensor;

a display device holder disposed on the base portion and configured to hold a display device;

a trigger configured to move the movable tip between the first position and the second position; and a retractable biasing device coupled to the trigger, wherein the trigger is configured to move between a default position and an actuated position, wherein the retractable biasing device is configured to move the trigger from the actuated position to the default position.

\* \* \* \* \*